United States Patent [19]

Incando

[11] Patent Number: 5,393,520

[45] Date of Patent: Feb. 28, 1995

[54] HAIR TREATMENT METHOD AND COMPOSITION

[76] Inventor: Peter A. Incando, 7640 Peerless, Orangevale, Calif. 95662

[21] Appl. No.: 76,558

[22] Filed: Jun. 11, 1993

[51] Int. Cl.⁶ .............................................. A61K 7/075
[52] U.S. Cl. ................... 424/70.13; 34/343; 34/348; 132/200; 132/209; 424/70.1
[58] Field of Search ............... 424/70; 132/200; 34/3

[56] References Cited

U.S. PATENT DOCUMENTS

| | | | |
|---|---|---|---|
| 4,220,167 | 9/1980 | Newell | 424/70 |
| 4,416,296 | 11/1983 | Meyers | 424/70 |
| 4,608,392 | 8/1986 | Jacquet et al. | 424/69 |
| 4,752,467 | 6/1988 | Konrad et al. | 424/70 |
| 4,983,383 | 1/1991 | Maksimoski et al. | 424/70 |
| 4,985,239 | 1/1991 | Yahagi et al. | 424/70 |
| 4,999,195 | 3/1991 | Hayes | 424/70 |
| 5,002,761 | 3/1991 | Mueller et al. | 424/70 |
| 5,006,331 | 4/1991 | Gaskin | 424/70 |

*Primary Examiner*—José G. Dees
*Assistant Examiner*—Dwayne C. Jones
*Attorney, Agent, or Firm*—Bernhard Kreten

[57] ABSTRACT

A method for treating hair is provided which includes the application of three compositions of matter with drying steps therebetween. A first and second composition are not less than 50% acetone, are not water soluble and penetrate deeply into the hair to reconstruct damaged hair. A third composition acts as an emollient and high-protein conditioner to revitalize the hair after its reconstruction with the first and second compositions.

15 Claims, 1 Drawing Sheet

HAIR TREATMENT METHOD AND COMPOSITION

FIELD OF THE INVENTION

The following invention relates to compositions of matter which are useful in treating damaged hair and methods for their application. More specifically, the following invention relates to methods for applying distinct hair treatment compositions in series, some of which include a solvent such as acetone as a major component and others which include emollients and protein based conditioners.

BACKGROUND OF THE INVENTION

When hair is treated harshly or is defective in some way, steps must be taken to reconstruct the damaged hair and return it to good health. Healthy hair is characterized by having strength and flexibility, being easily curled, and having sufficient elasticity to avoid breaking.

Various products are known in the art which attempt to reconstruct hair. Some of these products are termed "moisturizers" which remoisturize hair that is excessively dry. Some products add emollients to hair, making the hair soft and flexible. Other compositions are known which provide coatings of various types which merely cover a surface of each hair. Moisturizers and emollients are generally regarded as ineffective in healing damaged hair. Coatings merely cover the hair without any healing taking place. Thus, a need exists for some way to reconstruct damaged hair.

The compositions of this invention, when applied according to the method of this invention, reconstruct the damaged hair. Compositions utilized by this method are not water-soluble and thus are not stripped from the hair during the normal washing process. This allows the benefits of the present invention to reside longer in the hair. Accordingly, this invention results in hair which is reconstructed and more able to withstand the rigors of styling.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
|---|---|---|
| 4,220,167 | September 2, 1980 | Newell |
| 4,752,467 | June 21, 1988 | Konrad, et al |
| 4,985,239 | January 15, 1991 | Yahagi, et al |
| 4,983,383 | January 8, 1991 | Maksimoski, et al |
| 4,608,392 | August 26, 1986 | Jacquet, et al |
| 4,999,195 | March 12, 1991 | Hayes |
| 5,002,761 | March 26, 1991 | Mueller, el al |
| 5,006,331 | April 9, 1991 | Gaskin |

The patent to Newell teaches a method for restoring the moisture level of hair having a moisture deficiency. This invention is distinguishable from the teachings of Newell in that this invention reconstructs the hair rather than merely remoisturizing the hair and also in that the compositions utilized by this invention are distinguishable from the compositions taught by Newell.

The remainder of the prior art listed above, but not specifically distinguished, diverge even more starkly from this invention than the patent to Newell discussed above.

SUMMARY OF THE INVENTION

The method of this invention involves the application of three distinct compositions of matter to hair for revitalization of the hair. The hair treatment process includes initially thoroughly cleaning and drying the hair. The first composition is then applied to the hair and allowed to fully saturate the hair. The hair is then blown dry. Next, the second composition is applied sparingly to the ends of the hair. The hair is then blown dry a second time. These compositions are not water soluble and thus will not be removed from the hair by subsequent washing. After application of the first composition and the second composition, a third composition is applied to the hair which acts as a high protein content conditioner. The hair may then be dried in any manner or it may be styled.

Once the hair has gone through this three-composition treatment process, the hair is stronger and more elastic. The treatment process is most effective when repeated seven to fourteen days after the initial treatment. Retreatment is then performed on a periodic basis as needs of the hair require.

The first composition is approximately 80% acetone and also includes isopropanol, isobutane, 2-propanol-1-methoxyacetate, ethylene glycol monobutyl ether, nitrocellulose and fragrance. The second composition is approximately 60% acetone and also includes isobutane, isopropanol, 2-propanol-1-methoxyacetate, ethylene glycol monobutyl ether, nitrocellulose and fragrance.

The third composition includes extract of comfrey, mountain spring water, isopropyl alcohol, gink biloba and kelp, dicetyldimonium chloride, hydrolyzed keratin protein, ammonia, aloe vera gel, unprocessed artesian water, sodium PCA, humectants, benzophenone-4, panthenol, glycerine, solium lactate, propylparaben, PEG-75 lanolin oil, dimethicone, deionized water, nonoxynol-10, methylparaben, isodecane, DMDM hydantoin, propylene glycol, polymethoxy, oxycinnamate, bicyclic oxazolidine, fragrance and color, and lactic acid.

OBJECTS OF THE INVENTION

Accordingly, it is a primary object of the present invention to provide a method for treating damaged hair to effect revitalization of the hair.

Another further object of the present invention is to provide a method for hair treatment which adds volume and strength to fine limp hair.

Another further object of the present invention is to provide a method for hair treatment which adds texture and strength to thin fine hair.

Another further object of the present invention is to provide a composition of matter which can protect hair.

Another further object of the present invention is to provide a composition of matter which reduces breakage of hair which has been treated with chemical relaxers.

Another further object of the present invention is to provide a method for hair treatment which increases the ability of the hair to be curled.

Another further object of the present invention is to provide a method for hair treatment which mends and strengthens long hair that has damaged hair ends.

Another further object of the present invention is to provide a method of hair treatment which adds strength and shine to over-medicated hair.

Another further object of the present invention is to provide a composition of matter which, when applied to hair, penetrates down to the cortex of individual hairs.

Another further object of the present invention is to provide a composition of matter which, when applied to hair, amplifies the effectiveness of styling products later used on the hair.

Another further object of the present invention is to provide a method for hair treatment which adds strength and elasticity to hair.

Another further object of the present invention is to provide a method for hair treatment which keeps the hair from oxidizing, allowing the hair to maintain a color treatment for a longer duration.

Another further object of the present invention is to provide a method for hair treatment which mends damaged hair and bonds the hair to a solid length.

Another further object of the present invention is to provide a method for hair treatment which includes application of compositions which retard frizzing of the hair in high humidity conditions.

Another further object of the present invention is to provide a composition of matter which is not water soluble and will not wear away when applied to hair.

Another further object of the present invention is to provide compositions of matter which are easily fabricated and easy to handle and use.

Viewed from a first vantage point it is an object of this invention to provide a hair treatment composition comprised of between about 0.5% and 2.5% isopropanol, between about 75% and 85% acetone, between about 5% and 15% isobutane, between about 2.5% and 5% 2-propanol-1-methoxyacetate, between about 0.5% and 2.5% ethylene glycol monobutyl ether and between about 0.5% and 2.5% nitrocellulose.

Viewed from a second vantage point it is an object of this invention to provide a hair treatment composition which is non-water soluble and adds strength to hair consisting essentially of between about 0.5% and 2.5% isopropanol, between about 75% and 85% acetone, between about 5% and 15% isobutane, between about 2.5% and 5% 2-propanol-1-methoxyacetate, between about 0.5% and 2.5% ethylene glycol monobutyl ether and between about 0.5% and 2.5% nitrocellulose.

Viewed from a third vantage point it is an object of this invention to provide a hair treatment composition comprised of between about 1% and 5% isopropanol, between about 50% and 70% acetone, up to about 30% isobutane, between about 5% and 10% 2-propanol-1-methoxyacetate, between about 1% and 5% ethylene glycol monobutyl ether and between about 1% and 5% nitrocellulose.

Viewed from a fourth vantage point it is an object of this invention to provide a method for treating hair including the steps of applying a first composition to the hair to be treated comprised of not less than 75% acetone, drying the hair, applying a second composition to the hair to be treated comprised of not less than 50% acetone, drying the hair, applying a third composition to the hair to be treated and styling the hair.

These and other objects will be made manifest when considering the following detailed specification when taken in conjunction with the appended drawing figures.

DESCRIPTION OF PREFERRED EMBODIMENTS

Figure 1:
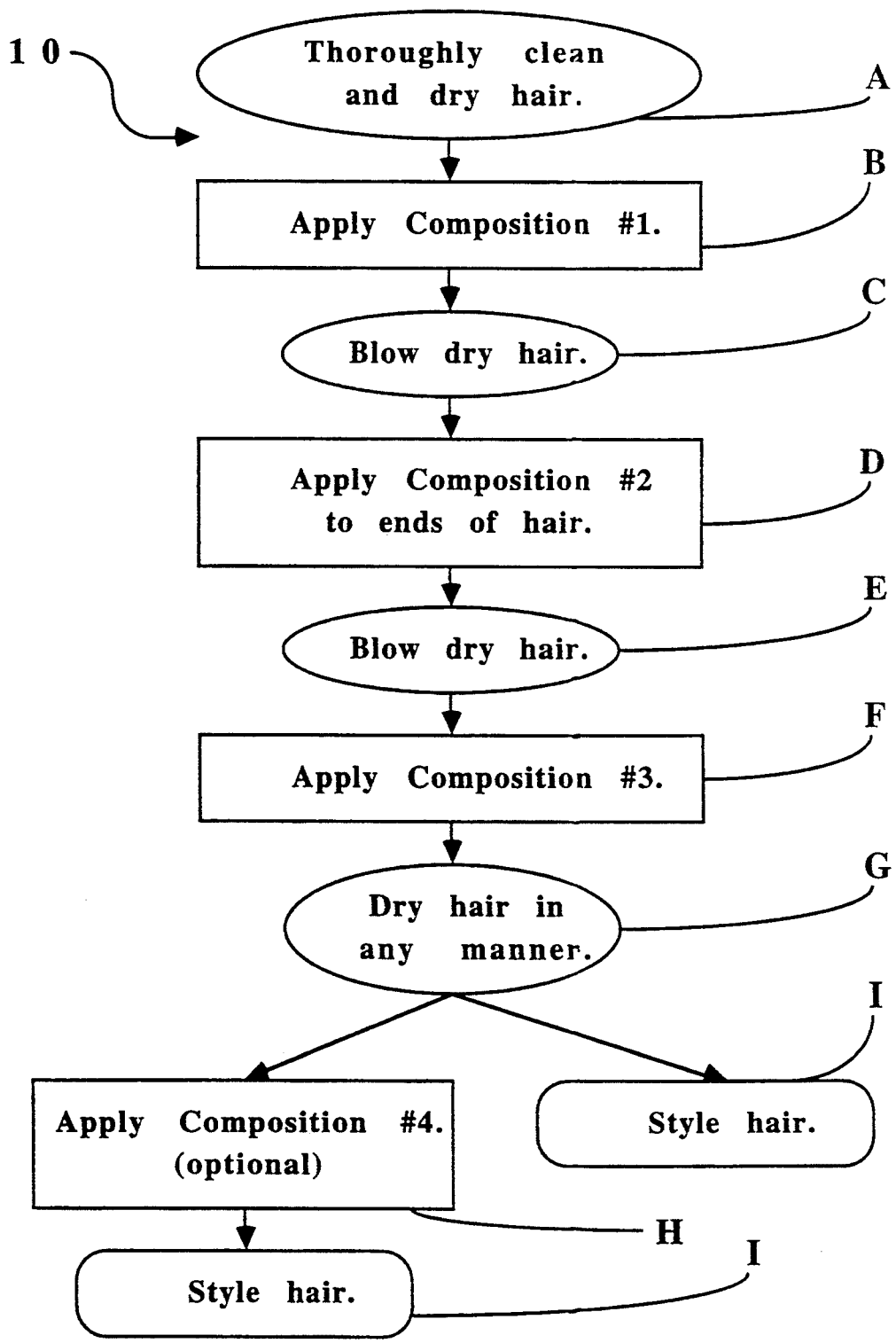
FIG. 1 is a diagram representing the individual steps involved in practicing the method of this invention.

Referring now to the drawing figure wherein like reference numerals refer to like elements throughout, a method for treating hair 10 and compositions of matter 1, 2, 3 to be used in the method 10 are disclosed. In essence, the hair treatment method 10 begins with thorough cleansing and drying of the hair (step A). Step A is then followed by: applying composition 1 to all of the hair to be treated (step B), applying composition 2 sparingly to ends of the hair (step D), and applying composition 3 to all of the hair (step F). Between the application of these compositions 1, 2, 3 the hair is dried (steps C, E, G). After the final composition has been applied the hair can be styled (step I).

More specifically, and referring in detail to FIG. 1, the hair to be treated is initially thoroughly cleansed and dried (step A). This cleaning process is preferably done with shampoo only so that the hair likely has no water soluble conditioners thereon. After step A the hair is ready to receive the treatments with the compositions of matter 1, 2, 3.

In step B composition 1 is applied to the hair. In essence, composition 1 is a non-water soluble solution such as one containing approximately 80% acetone. Other details of the exact preferred constituents contained within composition 1 are described in detail below. Composition 1 is preferably applied with an instrument which allows application of composition 1 directly to the hair. By directly applying composition 1 to the hair, as by daubing or spraying close to the hair, the evaporative quality of composition 1 is prevented from generating excessive fumes in the environment surrounding where the application of composition 1 is occurring. Utilization of an air purifier is still preferred, however.

Also, direct application of composition 1 allows the user to prevent composition 1 from coming into contact directly with the scalp. Composition 1 is preferably applied no closer than 2 inches from the scalp. Various additional precautions common in the art for other processes may also be taken to prevent composition 1 from coming into contact with the scalp. Also, utilization of a shield is advised to prevent composition 1 from coming into contact with the face and eyes of the person whose hair is being treated. Preferably, a towel is utilized to act as the shield.

Once the hair has been thoroughly saturated with composition 1, the hair is preferably blown dry, as represented by step C. This drying step C is preferably accomplished with medium heat from a blow dryer with a diffuser in place. Drying is continued until the hair is thoroughly dried.

While the exact mechanism by which composition 1 reconstructs hair could be the subject matter of some conjecture, it is believed that application of composition 1 has a deep penetrating cleansing effect on the hair. Composition 1 acts as a solvent breaking up and removing any chemicals which could not be removed by step A. Composition 1 is also believed to penetrate deep into the hair, entering a region referred to as the cortex, resulting in increased strength and flexibility of the hair.

Once the hair has been thoroughly dried by step C, the hair is sectioned into separate sections of approximately 50 square inches and composition 2 is applied to each section of the hair (step D). Preferably composition 2 is applied sparingly with a spray applicator and only to ends of the hair. The hair should be only slightly damp after application of composition 2.

Composition 2 is approximately 60% acetone and has a similar composition as that exhibited by composition 1. However, other constituents in composition 2 have approximately twice the concentration as that in composition 1. Further details of the constituents of composition 2 are described below. Composition 2 is best applied only to ends of the hair in that ends of the hair are often more damaged than portions of the hair closer to the scalp. This is often true because ends of the hair are older and have thus experienced more damage than portions of the hair near the scalp for a variety of reasons, such as from long-term coiffing. Composition 2 should also be applied in a manner which ensures that it will not come into contact with the scalp, face or eyes of the person whose hair is being treated. Precautions to avoid such hazardous contact preferably include those enunciated above with respect to step B.

It is believed that composition 2 provides further reconstruction of the hair, especially at ends of the hair. This reconstruction includes increasing hair thickness by as much as 30 to 50 percent. A definition for "ends of the hair" can be made on a case by case basis especially by a skilled beautician, but usually it is discernible in that the "ends" of the hair begin where a higher level of damage is identifiable. More highly damaged hair is characterized by such things as brittleness, lack of elasticity, weakness, and color change. Once step D has been performed and ends of the hair have been treated with composition 2, all of the hair will preferably have been reconstructed to an extent which corresponds to the damage which the hair had experienced. Step E is then performed, blowing dry the hair in a manner similar to that described above with respect to step C. Compositions 1 and 2 are both non-soluble in water. Thus, after step E compositions 1 and 2 remain in the hair until they wear away.

Once step E has been completed and compositions 1 and 2 have been applied to the hair, the hair is ready to receive composition 3 which acts as an emollient to condition and lubricate the rejuvenated hair. Composition 3 is then applied in step F by spraying generously over the hair. Composition 3 is specifically formulated to provide the hair with constituents which may have been stripped therefrom, thereby promoting revitalization of the hair. Composition 3 is water soluble and thus tends to lubricate the hair and restore flexibility and tensile strength but does not remove composition 1 or composition 2 from the hair.

The special formulation of composition 3 described in detail below, is believed to enter porous structures within the hair. These porous structures are believed to have been previously blocked in damaged hair before the applications of compositions 1 and 2 in steps B and D.

After the application of composition 3 in step F, the hair can be dried thoroughly and styled in any manner desired (steps G and I). Composition 3 acts as a high protein conditioner to further enhance the quality of the hair. After application of composition 3, the hair may then be styled in any manner (step I) with the benefits of the treatment method 10 available for the styling process. These benefits include decreased styling time when applying a permanent wave to the hair and when curling.

In an alternative embodiment, the compositions 1, 2, 3, can be applied in a sequence differing from the preferred embodiment. For instance, after composition 2 is applied (step D) and the hair is dried (step E), composition 3 can be applied (step F). Also, steps D and E can be skipped and composition 3 can be applied after applying composition 1 (step B) and drying (step C). In essence, so long as composition 1 or composition 2 (or both) is applied first and then composition 3 is applied, an effective treatment can occur.

Each of the compositions 1, 2, 3 is specifically formulated to perform portions of the method 10 enumerated above. It is believed that percentage amounts of each of the constituents can be varied somewhat without destroying the effectiveness of any of the compositions 1, 2, 3. However, the following specific enumeration of preferred constituent percentages and ranges for each of the compositions 1, 2, 3 is believed to be the most effective formulation for operation of the method 10 of this application.

| Composition 1 | | |
| --- | --- | --- |
| Constituent | Range (%) | Preferred (%) |
| Isopropanol | 0.5–2.5 | 1.555 |
| Acetone | 75–85 | 81.088 |
| Isobutane | 5–15 | 10.363 |
| 2-Propanol-1-MethoxyAcetate | 2.5–5 | 3.886 |
| Ethylene Glycol Monobutyl Ether | 0.5–2.5 | 1.555 |
| Nitrocellulose | 0.5–2.5 | 1.555 |
| Fragrance | trace | trace |

| Composition 2 | | |
| --- | --- | --- |
| Constituent | Range (%) | Preferred (%) |
| Isopropanol | 1–5 | 3.109 |
| Acetone | 50–70 | 62.176 |
| Isobutane | 10–30 | 20.725 |
| 2-Propanol-1-MethoxyAcetate | 5–10 | 7.772 |
| Ethylene Glycol Monobutyl Ether | 1–5 | 3.109 |
| Nitrocellulose | 1–5 | 3.109 |
| Fragrance | trace | trace |

| Composition 3 | | |
| --- | --- | --- |
| Constituent | Range | Preferred (%) |
| Extract of Comfrey | 5.25%–10.25% | 7.75 |
| Mountain Spring Water | 4.85%–9.85% | 7.35 |
| Isopropyl Alcohol | 3.75%–8.75% | 6.25 |
| Gink Biloba & Kelp | 3.5%–8.5% | 6.00 |
| Dicetyldimonium Chloride | 3.25%–8.25% | 5.75 |
| Hydrolyzed Keratin Protein | 3.0%–8.0% | 5.50 |
| Ammonia | 2.75%–7.75% | 5.25 |
| Aloe Vera Gel | 2.50%–7.50% | 5.00 |
| Artesian Water Unprocessed | 2.25%–7.25% | 4.75 |
| Sodium PCA | 2.10%–7.10% | 4.60 |
| Humectants | 2.0%–7.0% | 4.50 |
| Benzophenone-4 | 1.50%–6.50% | 4.00 |
| Panthenol | 1.25%–6.25% | 3.75 |
| Glycerine | 1.0%–6.0% | 3.50 |
| Solium Lactate | 0.80%–5.80% | 3.30 |
| Propylparaben | 0.60%–5.60% | 3.10 |
| PEG-75 Lanolin Oil | 0.50%–5.50% | 3.00 |
| Dimethicone | 0.30%–5.30% | 2.80 |
| Deionized Water | 0.25%–5.25% | 2.75 |
| Nonoxynol-10 | 0.25%–4.75% | 2.50 |
| Methylparaben | 0.25%–3.25% | 2.00 |
| Isodecane | 0.25%–3.25% | 1.75 |
| DMDM Hydantoin | 0.25%–2.25% | 1.25 |

| | Composition 3 | |
|---|---|---|
| Constituent | Range | Preferred (%) |
| Propylene Glycol | 0.25%–1.75% | 1.00 |
| Polymethoxy | 0.2%–1.4% | .80 |
| Oxycinnamate | 0.15%–1.35% | .75 |
| Bicyclic Oxazolidine | 0.1%–0.9% | .50 |
| Fragrance & Color | 0.05%–0.65% | .35 |
| Lactic Acid | 0.05%–0.35% | .20 |

The isobutane contained within products 1 and 2 is believed to substantially dissipate into the atmosphere upon ejection during the spraying of either composition 1 or composition 2. Thus, the constituents of composition 1 and composition 2 which actually contact the hair likely have a much smaller percentage of isobutane than that contained within compositions 1 and 2 before their ejection and application to the hair. Thus, a range of composition of isobutane in compositions 1 and 2 could extend down to 0% under certain conditions.

Moreover, having thus described the invention, it should be apparent that numerous modifications and adaptations may be resorted to without departing from the scope and fair meaning of the instant invention as set forth hereinabove and as described hereinbelow by the claims.

I claim:

1. A hair treatment composition comprised of:
   a) between about 0.5% and 2.5% isopropanol;
   b) between about 75% and 85% acetone;
   c) between about 5% and 15% isobutane;
   d) between about 2.5% and 5% 2-propanol-1-methoxyacetate;
   e) between about 0.5% and 2.5% ethylene glycol monobutyl ether;
   f) between about 0.5% and 2.5% nitrocellulose.

2. The composition of claim 1 wherein said composition includes:
   between about 1% and 2% isopropanol;
   between about 78% and 82% acetone;
   between about 8% and 12% isobutane;
   between about 3% and 4.5% 2-propanol-1-methoxyacetate;
   between about 1% and 2% ethylene glycol monobutyl ether; and
   between about 1% and 2% nitrocellulose.

3. A hair treatment composition which is non-water soluble and adds strength to hair consisting essentially of:
   a) between about 0.5% and 2.5% isopropanol;
   b) between about 75% and 85% acetone;
   c) between about 5% and 15% isobutane;
   d) between about 2.5% and 5% 2-propanol-1-methoxyacetate;
   e) between about 0.5% and 2.5% ethylene glycol monobutyl ether;
   f) between about 0.5% and 2.5% nitrocellulose.

4. The hair treatment composition of claim 3 wherein said composition consists essentially of:
   between about 1% and 2% isopropanol;
   between about 78% and 82% acetone;
   between about 8% and 12% isobutane;
   between about 3% and 4.5% 2-propanol-1-methoxyacetate;
   between about 1% and 2% ethylene glycol monobutyl ether; and
   between about 1% and 2% nitrocellulose.

5. A hair treatment composition comprised of:
   a) between about 1% and 5% isopropanol;
   b) between about 50% and 70% acetone;
   c) up to about 30% isobutane;
   d) between about 5% and 10% 2-propanol-1-methoxyacetate;
   e) between about 1% and 5% ethylene glycol monobutyl ether;
   f) between about 1% and 5% nitrocellulose.

6. The composition of claim 5 wherein said composition includes:
   a) between 2 and 4% isopropanol,
   b) between 55 and 65% acetone,
   c) up to 20% isobutane,
   d) between 6% and 9% 2-propanol-1-methoxyacetate,
   e) between about 2% and 4% ethylene glycol monobutyl ether, and
   f) between 2% and 4% nitrocellulose.

7. A method for treating the natural hair borne by a person, including the steps of:
   applying an acetone based non-water soluble composition to the hair,
   drying the hair, and
   applying a water-soluble conditioner to the hair.

8. A method for treating the natural hair borne by a person, including the steps of:
   applying a non-water soluble composition to the hair,
   drying the hair,
   applying a water-soluble conditioner to the hair,
   wherein said applying a non water-soluble solvent step further includes the steps of:
      applying a first composition to the hair to be treated comprised of not less than 75% acetone,
      drying the hair,
      applying a second composition to the hair to be treated comprised of not less than 50% acetone, and
      drying the hair.

9. The method of claim 8 including the further step of forming the first composition to include between about 0.5% and 2.5% isopropanol, between about 5% and 15% isobutane, between about 2.5% and 5% 2-proponol-1-methoxyacetate, between about 0.5% and 2.5% ethylene glycol monobutol ether, and between about 0.5% and 2.5% nitrocellulose.

10. The method of claim 9 including the further step of forming the second composition to include between about 1% and 5% isopropanol, up to about 30% isobutane, between about 5% and 10% 2-propanol-1-methoxyacetate, between about 1% and 5% ethylene glycol monobutol ether and between about 1% and 5% nitrocellulose.

11. The method of claim 10 wherein said drying steps include the step of heating the hair with a hot air source.

12. The method of claim 11 wherein said applying a second composition step includes applying the second composition only to ends of the hair distant from the scalp.

13. The method of claim 12 wherein said method of treating hair is repeated a second time after at least two days have elapsed.

14. The method of claim 13 wherein each of said applying steps occurs with hair that has been first thoroughly dried.

15. The method of claim 14 wherein said applying a first composition step includes dabbing the first composition onto the hair until the hair is saturated from ends of the hair to within three inches of the scalp.

* * * * *